United States Patent
Pohl et al.

(10) Patent No.: US 10,624,589 B2
(45) Date of Patent: Apr. 21, 2020

(54) METHOD AND APPARATUS VISUALIZING A MEDICAL OBJECT

(71) Applicant: Siemens Healthcare GmbH, Erlangen (DE)

(72) Inventors: Thomas Pohl, Marloffstein (DE); Rainer Schneider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 12 days.

(21) Appl. No.: 16/015,577

(22) Filed: Jun. 22, 2018

(65) Prior Publication Data
US 2018/0368783 A1  Dec. 27, 2018

(30) Foreign Application Priority Data
Jun. 22, 2017  (DE) .................. 10 2017 210 528

(51) Int. Cl.
| | |
|---|---|
| *A61B 5/00* | (2006.01) |
| *A61B 5/055* | (2006.01) |
| *G06T 11/00* | (2006.01) |
| *G06K 9/62* | (2006.01) |
| *G01R 33/36* | (2006.01) |

(Continued)

(52) U.S. Cl.
CPC ............ *A61B 5/7425* (2013.01); *A61B 5/055* (2013.01); *A61B 5/06* (2013.01); *G01R 33/287* (2013.01); *G01R 33/3664* (2013.01); *G01R 33/5608* (2013.01); *G06K 9/6204* (2013.01); *G06T 11/001* (2013.01); *G06T 11/60* (2013.01); *A61B 2576/00* (2013.01); *G01R 33/4835* (2013.01); *G01R 33/56341* (2013.01);

*G06K 2209/057* (2013.01); *G06K 2209/09* (2013.01); *G06T 2210/41* (2013.01)

(58) Field of Classification Search
CPC .... A61B 5/7425; A61B 5/055; G01R 33/287; G01R 33/3664; G06K 9/6204; G06K 2209/057; G06K 2209/09; G06T 11/001; G06T 2210/41
See application file for complete search history.

(56) References Cited

U.S. PATENT DOCUMENTS

| | | | | |
|---|---|---|---|---|
| 2014/0229881 A1* | 8/2014 | Schadewaldt | ......... | G06F 3/0484 715/771 |
| 2015/0089365 A1* | 3/2015 | Zhao | ..................... | G06F 19/321 715/708 |

(Continued)

OTHER PUBLICATIONS

Campbell-Washburn et al., "Positive contrast spiral imaging for visualization of commercial nitinol guidewires with reduced heating," Journal of Cardiovascular Magnetic Resonance, vol. 17:114 (2015).

(Continued)

*Primary Examiner* — Chong Wu
(74) *Attorney, Agent, or Firm* — Schiff Hardin LLP

(57) ABSTRACT

In a method and apparatus for visualizing the position of a medical object in a body of an examination object, a stack of sectional images through the body, acquired by operation of a magnetic resonance imaging system, is provided to a processor, which implements sectional-image-specific pixel coding of the sectional images. This is followed by the creation of a combination image composed of a combination of a number of coded sectional images from the stack, and representation of the combination image.

13 Claims, 6 Drawing Sheets

(51) Int. Cl.
  G01R 33/28 (2006.01)
  A61B 5/06 (2006.01)
  G01R 33/56 (2006.01)
  G06T 11/60 (2006.01)
  G01R 33/563 (2006.01)
  G01R 33/483 (2006.01)

(56) References Cited

U.S. PATENT DOCUMENTS

| | | |
|---|---|---|
| 2015/0148660 A1 | 5/2015 | Weiss et al. |
| 2015/0258349 A1 | 9/2015 | Grodzki et al. |
| 2015/0294082 A1 | 10/2015 | Passerini et al. |
| 2016/0071267 A1* | 3/2016 | Wakai .................. A61B 6/5211 382/128 |
| 2016/0073925 A1 | 3/2016 | Grodzki et al. |
| 2016/0073926 A1 | 3/2016 | Grodzki et al. |
| 2017/0042632 A1 | 2/2017 | Rothgang et al. |

OTHER PUBLICATIONS

Stuber et al., "Positive Contrast Visualization of Iron Oxide-Labeled Stem Cells using Inversion-Recovery With ON-Resonant Water Suppression (IRON)," Magnetic Resonance in Medicine, vol. 58, pp. 1072-1077 (2007).

Seppenwoolde et al., "Passive Tracking Exploiting Local Signal Conservation: The White Marker Phenomenon," Magnetic Resonance in Medicine, vol. 50, pp. 784-790 (2003).

Ratnayaka et al., "Real-time MRI-guided right heart catheterization in adults using passive catheters," European Heart Journal, vol. 34, pp. 380-388 (2013).

Duerk et al., "A brief review of hardware for catheter tracking in magnetic resonance imaging," Magnetic Resonance Materials in Physics, Biology and Medicine, vol. 13, pp. 199-208 (2002).

* cited by examiner

METHOD AND APPARATUS VISUALIZING A MEDICAL OBJECT

BACKGROUND OF THE INVENTION

Field of the Invention

The invention concerns a method for visualizing the position of a medical object, a visualization apparatus relating thereto, a control computer for controlling a magnetic resonance imaging system, and a magnetic resonance imaging system having such a control computer.

Description of the Prior Art

In a magnetic resonance system (apparatus), also known as a magnetic resonance imaging system, the body to be examined is typically exposed to a relatively high basic magnetic field of 1, 5, 3 or 7 tesla, for example, by a basic field magnet. In addition, magnetic field gradients are applied by a gradient coil arrangement. Radio-frequency excitation signals (RF signals) are then emitted via a radio-frequency transmission system by suitable antennas, so as to cause the nuclear spins of specific atoms to be excited into resonance by the radio-frequency field, and thus deflected through a defined flip angle with respect to the magnetic field lines of the basic magnetic field. Upon relaxation of the nuclear spins, radio-frequency signals, so-called magnetic resonance signals, are emitted, and are received by suitable reception antennas, and then processed further. Finally, the desired image data can be reconstructed from the raw data acquired in this way.

Accordingly, it is necessary to transmit a specific pulse sequence for a specific scan, the pulse sequence being a train of radio-frequency pulses, in particular excitation pulses and refocusing pulses, as well as, matched thereto, gradient pulses that are to be transmitted in a coordinated manner in different spatial directions. Read-out windows, matched with respect to time, must be set to specify the time periods in which the induced magnetic resonance signals are acquired. A decisive factor for the imaging is the timing within the sequence, i.e. which pulses succeed one another at which time intervals. A large number of control parameters is generally defined in a so-called scan protocol, which is created in advance and can be retrieved from a memory for a specific scan, and if necessary modified in situ by the operator, who can specify additional control parameters, such as a specific inter-slice distance of a stack of slices that are to be scanned, a slice thickness, etc. A pulse sequence, which is also referred to as a scan sequence, is then calculated on the basis of all these control parameters.

In view of the relatively strict timing of the pulse sequence, it is necessary to estimate a scanning time for the recording of image data with a duration that cannot be arbitrarily reduced.

Consequently, recordings of multiple slices to cover large body volumes are not generally possible in real time. It is thus not possible, or possible only with a significant technical outlay, to track a medical object, such as a catheter, moving through the body or to check the current position of such an object. Recording larger 3D volumes or thicker slices of 1 to 2 cm, instead of a number of thinner slices of 1 to 3 mm, would not be helpful, since these are also time-consuming to create and there is an additional risk that the object, in particular a thin catheter, can no longer be recognized because its signal component (signal contribution in the overall image) is subsumed in the thick volume or thick slice.

Methods in which magnetic resonance imaging is performed during interventional surgery are known from DE102015215476A1, US20150294082A1, US 20150258349A1, DE102014218445A1 and DE102014218454A1.

SUMMARY OF THE INVENTION

An object of the present invention is to provide a method, a visualization apparatus and a corresponding control computer for controlling a magnetic resonance imaging system, with which the above-described drawbacks can be avoided.

In the method according to the invention for visualizing the position of a medical object, the user is provided with a simple way of displaying or recognizing a position of this object, for example of the catheter, in the body. The visualizing method according to the invention has the following basic steps (a) through (d).

(a) Provision of a stack of sectional images through the body recorded by the scanner of a magnetic resonance imaging system. As described above, such sectional images are recorded in a number of slices of the body and are available, first, as recorded (raw) data and, following conventional processing, as image data. At least some of the sectional images contain the medical object or a portion thereof. The term "stack" means that the image planes of the sectional images, i.e. the slice planes in which these images were recorded, lie parallel to one another and depict the images in the body in successive slice planes. The medical object is thus within the stack, but may not be present in each and every sectional image in the stack.

At least two, particularly preferably at least three, sectional images are recorded, in particular images from three directly adjacent slice planes. Care should be taken to ensure that the slice plane extends in a plane approximately parallel to the longitudinal axis of the medical object, as explained in more detail below.

(b) Next, optionally after preprocessing of the images, sectional-image-specific coding of a least a part, preferably at least two, of the different sectional images takes place. This sectional-image-specific coding is a visual coding, particularly preferably color coding. Pixels, in particular all the pixels, of a coded sectional image are given a coding uniquely assigned to that sectional image, at least when they have a specific intensity. The assigned coding characterizes the sectional images preferably such that the relative position of a sectional image within the stack under consideration always has a coding comparable to the other sectional images considered. For example, the respective uppermost sectional images in a (partial) stack under consideration are coded in a comparable way as are the respective lowermost sectional images.

The assignment of the unique coding to the individual sectional images is preferably freely chosen. Since the sectional images generally consist of grayscale values, the individual sectional images are labeled, for example by coloring with different colors. For example, in the case of three sectional images, the uppermost sectional image of the stack is colored red, the middle one is colored white, and the lowermost one is colored blue. This sequence can also be freely chosen.

(c) This is followed by the creation of a combination image by combining a number of the coded sectional images from the stack. Depending upon the type of combination, this combination can also be called a type of projection and the resulting image called a "projection image". Preferably a projection direction is specified that, looking through the stack from above, extends orthogonally to the sectional images and combines all the regions (pixels) lying in sequence in this projection direction with one another. In a particularly preferred case, in which the sectional images each have the same format and the same number of pixels, pixels at the respective same positions in the sectional images (same image coordinates) are combined with one another, or in each case there is a projection of pixels that each have identical positions in the different sectional images.

(d) Then follows a representation of the combination image or the projection image. Even though it is two-dimensional, due to the image-specific coding, it is simple to derive the position of the medical instrument from this combination image. On the basis of the above example with the three sectional images, wherein the uppermost is coded red, the middle one is coded white and the lowermost is coded blue, a medical object that is represented as white is known to be located exactly in the interior of the stack, i.e. exactly between the outermost images; if the medical object is colored blue or red, it is known to be located at the edge of the stack, wherein red coloring indicates it is too high and blue coloring that it is located too far down in the stack. Although it is true that no direct conclusions can be drawn regarding the position of the medical object in the body from the coded representation of the object on its own, the person using the magnetic resonance imaging system learns how the slice planes should be tracked for further observation of the object. Moreover, it is easy to derive the position of the object in the body from the other image information in the combination image, wherein, due to their coding, the image regions of the body structures also contain depth information, even though this is only a 2D-representation.

The invention is suitable both for locating the medical object in a body and aligning the slice planes in accordance with the dimensions of the object and for tracking the object as it moves through the body. This is achieved by the multiple application of the method, i.e. repeated recording of a stack from sectional images, coding and creation of the corresponding combination image. The combination image enables the magnetic resonance imaging system to be controlled and then the next stack recorded.

Since only at least two, or preferably at least three, sectional images have to be recorded on each pass and this requires a relatively short time, even virtually real-time tracking is possible. In the case of quicker scanning methods, it is also possible to record more sectional images, thus permitting better classification of the object, but the combination image is preferably not formed from too many sectional images. Particularly preferably, not more than 10 sectional images are combined. For up to 10 images, it is possible to ensure that depth information does not become blurred as a result of the different coding.

A visualization apparatus according to the invention for visualizing the position of a medical object in a body, in particular according to the method according to the invention, has the following basic components (a) through (d).

(a) An image interface that provides a stack of sectional images recorded by a magnetic resonance imaging system. This can be a pure software interface that accepts data from other units or software modules, for example an image reconstruction computer. This is the case when the visualization apparatus is itself part of a control computer of the magnetic resonance imaging system.

(b) A coding processor that receives the stack of sectional images from the image interface, and that performs sectional-image-specific coding of at least some, preferably at least two, of the different sectional images. This coding processor operates, as described above, to code pixels of a sectional image with coding assigned to the sectional image, or coding characteristic of this sectional image as explained above. This can take place by characteristic coloring of the sectional images that permits conclusions to be made regarding the position of the sectional images in the stack and, when a number of stacks is considered, contains comparable coding types for corresponding positions of the sectional images in the stack.

(c) An image-creating processor that generates a combination image from a combination of the coded sectional images from the stack, as described above.

The coding processor and the image-creating processor can be part of a common computer that codes and combines the pixels by calculation and conversion, or makes a projection.

(d) An output interface at which the combination image is visually shown.

The apparatus can additionally communicate with another output interface, such as a display. If this is part of a medical system, such as a magnetic resonance imaging system, it is also able to use output interfaces of the system as the aforementioned output interface.

The visualization apparatus preferably also has a recognition processor that performs an automatic recognition algorithm in order to identify the medical object. Such a recognition unit automatically recognizes the medical object in image data generated by the magnetic resonance imaging system or in the sectional images or the combination image.

A control computer according to the invention for controlling a magnetic resonance imaging system has a visualization apparatus according to the invention, and preferably the aforementioned recognition processor. It is also particularly preferably designed for automatic tracking of the recording of a further stack of sectional images so that the medical object is substantially acquired (preferably at least with the most relevant part, generally a front part with which the object is introduced into the body) from the further stack of sectional images, i.e. is recognizable in at least one of the sectional images.

Preferably, the tracking is performed such that the medical object is located substantially inside the further stack of sectional images. Where the stack is concerned, "inside" means that the medical object is substantially visible in a number of sectional images lying between the sectional images at the upper and lower edge of the stack. Here, "number" can also be considered to mean a single sectional image. In the above example with three sectional images, therefore, the medical object should preferably always be visible substantially in the middle sectional image. If this is not the case, the recording position of the next stack of sectional images is preferably suitable adapted by the control device.

A magnetic resonance imaging system according to the invention has a control computer according to the invention.

In the case of a stack according to the invention of at least three sectional images recorded by means of a magnetic resonance imaging system, at least two of these sectional images have a coding in a form such that pixels of each coded sectional image contain coding that characterizes the sectional image in question or its position in the stack.

It is not mandatory for all the sectional images to be coded differently. Furthermore, the retention of the original state, for example no coloration, of some sectional images in a stack can be considered to be coding inside the stack if other sectional images of the stack are coded such that they differ from the sectional images that retain the original state. For example, it may be sufficient for only the outer sectional images in the stack to be coded and for the inner sectional images still to retain their gray tones. In particular, the inner sectional images in the stack can all have the same coding, for example white, or be uncoded in gray tones, while the uppermost sectional image in the stack is blue and the lowermost red.

However, it is preferable for all the sectional images to have different coding, because, in the case of more than three sectional images, this also enables particularly good recognition of the position of the medical object inside the stack and its orientation can be determined more accurately. For example, in the case of five sectional images, the color progression of the coding can be blue for the uppermost sectional image, then light blue, followed by white for the middle sectional image, then light red and finally red for the lowermost sectional image.

Another possible type of color coding is based on the standardized color coding used in diffusion tensor imaging. Diffusion tensor imaging (abbreviated to DTI for diffusion tensor imaging or DT-MRI for diffusion tensor magnetic resonance imaging) is a commonly used variant of diffusion-weighted magnetic resonance imaging that also includes the directional dependence of diffusion. This variant acquires not only the intensity, but also a tensor describing the three-dimensional diffusion behavior for each image point. The color coding is preferably dependent upon the anatomical orientation of the stack. Herein, each of the three directions is assigned one of the basic colors red, green and blue, which are mixed in the case of directions lying in-between. Image points without any clear principal direction can be shown as gray. Preference is given to red coding in the direction left-right, green coding in the direction anterior-superior and blue coding in the direction inferior-superior.

The greater part of the aforementioned components of the visualization apparatus and/or the control computer, in particular the coding processor and the image-creating processor and possibly the optional recognition processor, can be implemented wholly or partially in the form of software modules in a processor of a corresponding control computer. An implementation largely as software has the advantage that control units previously in use can also be upgraded in a simple manner by means of a software update in order to operate in the manner according to the invention. In this respect, the aforementioned object is also achieved by a computer-readable data storage medium encoded with program code that, when the storage medium is loaded a visualizing computer or a control computer of a magnetic resonance imaging system, causes carry out any or all embodiments of the method according to the invention to be implemented when the program code is executed in the visualizing computer or control computer. In addition to the computer code, additional items such as documentation and/or additional components and hardware components, such as hardware keys (dongles etc.), can be provided for using the code.

The computer-readable storage medium can be, for example, a memory stick, a hard disk or another kind of transportable or integrated data carrier on which the program code is stored.

The sectional-image-specific coding can take place in different ways. However, preference is given to an embodiment of the method according to the invention with which the sectional-image-specific coding is, as mentioned above, visual coding.

The magnetic-resonance signal is typically represented as a variation of the brightness signal, often by grayscale graphics. Therefore, color coding is preferable for the depth information, i.e. the information on the sectional image or position thereof in the stack. With color coding of a sectional image, the pixels of this sectional image are preferably color coded with a color assigned to the respective sectional image or the position thereof in the stack and which hence characterizes the respective sectional image or said position of the sectional image. For clarification, reference is made to the above example with three sectional images with which the uppermost sectional image was always given blue coding, the lowermost sectional image was always given red coding the middle sectional image was always given white coding.

However, in principle, it would also possible to transpose the above-described coding, namely in a form in which the magnetic-resonance signal is represented in the form of colored image information and the depth information is brightness-coded.

Generally, it would also be possible for the two types of information named above, image information and depth information, to be coded in the same way but with different colors or intensity regions or for the types of representation or coding to overlap. For example, the magnetic-resonance signal can be represented in the red channel and the coding of sectional images can lie in the blue channel.

Preferably, to obtain the combination image, the pixels of different sectional images lying in a predetermined projection direction one after the other or one on top of the other with a predetermined combination function are combined with one another. As mentioned above, a projection direction orthogonal to the sectional images of the stack is preferable, wherein combination of the respective pixels arranged one on top of the other (pixels with same image coordinates in the respective sectional images) takes place at the same time as the assignment of the respective coding of the pixels in question.

The combination function preferably includes an intensity-value-dependent projection, such as, for example, a maximum- or minimum-intensity projection, and a projection of pixels in a predetermined intensity interval or a peak-to-peak projection, i.e. a projection with which the maximum intensity difference of the pixels is calculated.

According to one preferred combination function, a mask image, for example a color mask, is created from the coded sectional images and combined with a projection image, which is in particular based on the uncoded sectional images. Herein, this mask image includes the coding information for the combined pixels of the sectional images in question and the projection image includes intensity information for the combined pixels.

According to one preferred embodiment, to this end, the pixels of sectional images according to the invention are coded with the coding assigned to the respective sectional image and a mask image is created in which each pixel at a specific position includes proportional coding information for pixels of the sectional images at the corresponding position with respect to its intensity. In particular, each pixel of the mask image is standardized with respect to overall intensity so that the intensity of all the pixels of the mask image is the same. In the example with three sectional images, each pixel triad in an image coordinate of the three sectional images is added with respect to its color value to a mask image pixel and preferably standardized to specific intensity. This produces a mask image with which the color of each pixel indicates the degree of the intensity influence of the individual sectional images at this position. The sectional images can be inverted before coding if this appears advisable.

According to another preferred embodiment, the pixels of the sectional images are projected onto one another in a suitable manner and a projection image is created with which each pixel of the projection image indicates the pixel or pixels of the sectional images that are dominant there with respect to their intensity. This is performed by the aforementioned types of projection, for example with peak-to-peak projection.

In a preferred further step, the mask image and the projection image are now combined with one another, for example by multiplying the values of the individual pixels.

Preferably, the values of the pixels of the sectional images and/or the type of projection are adapted to anatomical structures and/or the medical object. Herein, specific anatomical structures and/or the medical object are preferably represented with different colors in each sectional image and characterized thereby. An example of this was given above in the description of different types of visual coding. In this case, a preferred type of visual coding for the pixels of the sectional images or information in the sectional image planes is preferably brightness-coding.

Preferably, before the combination of the coded sectional images, in particular before the coding, further graphical preprocessing of the sectional images is performed. Herein preference is given to graphical preprocessing from the group including edge enhancement ("edge detection filters" such as, for example, Sobel, Prewitt compass, Roberts, Laplace, differentia), posterization, deflickering, soft focus, sharpening, inversion, brightness change and contrast change. It is also possible to use a Hough transform during preprocessing, which—as explained below—can be advantageous for the automatic recognition of image elements.

Preferably, as mentioned above, automatic recognition of the medical object takes place. To this end, the visualization apparatus or the control device preferably comprises a recognition unit.

Recognition of the medical object is preferably based on a comparison with reference images. Sectional images without the medical object are, for example, subtracted from sectional images with the medical object with respect to the intensity values of pixels. It is also preferable to use the Hough transform for recognition. For example, utilizing knowledge of the geometry of the medical object, a Hough transform could be used to recognize and highlight straight lines, circles or other geometric shapes. It is also possible for the geometry of the medical object to be combined with factors, in particular when the object is equipped with a labeling element such as, for example, a contrast medium or small MR receiver coils (coils for recognition by means of a magnetic resonance imaging system). The regions of such labeling elements can be recognized in the grayscale image as particularly light points and can be used as distinctive starting/end points with active contour algorithms (algorithms for active contour recognition).

Automatic recognition of elements, for example the medical object, in the individual images can also be performed before the creation of the combination image in order to utilize the information obtained herein during the combination, for example for restriction to the relevant image areas around the medical object during the combination.

Preferably, as also mentioned above, automatic tracking of the slice planes takes place during the recording of a further stack of sectional images. Herein, this tracking is preferably performed such that the position of the medical object in the interior of the stack or at the edge thereof is ascertained and, for a further recording of a stack, the planes of the sectional images are changed such that the position of the medical object ascertained in this way moves further toward the middle of the newly recorded stack or is selected as a new middle point. Particularly preferably, the slice planes are selected such that the medical object is substantially located inside the further stack of sectional images, i.e. not at the edge of the stack but somewhere in the interior thereof. In the case of three sectional images, this would be the middle sectional image, in the case of seven sectional images, with the sectional images 1 and 7 at the edge, it would be one or more of the sectional images 2 to 6.

Preferably, alignment of the orientation of the sectional images is performed such that an axis of greatest extent of the medical object whose probable route is specified, for example, by the course of a hollow organ into which the object in introduced, substantially extends in the plane of the sectional images. Herein, the term "substantially" means that any tilting of the plane of the sectional images with respect to this axis of the medical object is less than 30°, more preferably less than 10°, particularly preferably less than 5°. The goal is that the object should be aligned parallel to the slice planes. Herein, preferably automatic tracking of the orientation of the sectional images is performed in conformity with the aim of achieving as uniform as possible coding of the pixels representing the medical object. The term "as uniform as possible coding" relates to the change of coding undergone by the medical object when it lies obliquely to the slice plane and is hence partially represented in adjacent sectional images and should be uniform to the extent that the afore-mentioned maximum tilting (30° or 10°, or 5°) is not exceeded. In the example with the three sectional images in red, white and blue, an obliquely arranged elongated medical object would, for example, be red at one end, white in the middle and blue at the other end. As the length of the medical object and the spacing of the slice planes are known, the angle of tilting can be determined from the change in the coding.

Preferably, graphical post-processing of the combination image is performed in order to improve the representation of the medical object. This is based on one or more of the following assumptions.

(a) No overlapping of structures of the medical object in two adjacent sectional images should take place. This would, for example, be the case if the medical object is thinner than the spacing between two sectional images and lies parallel to the slice planes.

(b) The medical object should have a continuous contour. This is the case, if the object consists of a coherent body; this applies to the majority of medical objects.

(c) The medical object should have a uniform gradient over its contour. This would be the case if the object has a uniform surface without projections or indentations. For example, a uniform gradient may be expected along a catheter, wherein, perpendicular to its axis, it is clearly demarcated from the surrounding tissue, in particular at its tip.

Preferably, at least on the first acquisition or "initial recording" before or at the start of an intervention in which the object is introduced into the body, i.e. at the start of the scanning sequence, the position of the stack of sectional images is especially selected in order to increase the probability of the object also being acquired from the slice stack in the initial recording. Here, the location in the body at which the sectional images are recorded, and the orientation thereof can preferably be determined after suspected position of the medical object so that it lies in the interior of the stack. The orientation of the sectional images is selected such that it corresponds to the suspected orientation of a longest extension of the medical object. If, for example, the medical object is to be located in or introduced into a hollow organ, such as a blood vessel, the approximate position of the hollow organ or blood vessel and the orientation thereof in the body is known from previous scans or general knowledge of human anatomy. Hence, the sectional images can be recorded selectively at the site of this hollow organ with an orientation at which the hollow organ extends in the plane of the sectional images. The medical instrument will then be located at a good position in stack with a high degree of probability. Therefore, for the first recording, for example, more slice images will be taken than subsequently when the orientation or position of the object is already known from the previous scan. This initial recording is, for example, anyway generally made at the time when the time of the scan is still uncritical and it is possible to spend plenty of time on selecting a suitable position and orientation.

With this procedure, the stack preferably initially has more sectional images than are intended to be used in the combination image (the first recording). This enables a plurality of initial combination images to be created from respective adjacent coded sectional images. Preferably, corresponding coding is always used for the respective sectional images so that the x-th sectional image always has comparable coding for different combination images, i.e. depending on its position in the stack, one and the same sectional image is coded differently for different combination images.

On the initial combination images, the medical object is localized and the initial combination image selected with which the medical object lies inside the stack. The respective settings that were present during the recording of the sectional images in question for the selected initial combination image are taken into account as settings for the recording of the next stack.

A significant advantage of the method is that it is only necessary to record a few sectional images with a small thickness, for example thicknesses of about 1 to 3 mm. Large-volume, time-intensive recordings, for example in the ranges of from 1 to 2 cm, are not necessary.

DESCRIPTION OF THE PREFERRED EMBODIMENTS

Figure 1:
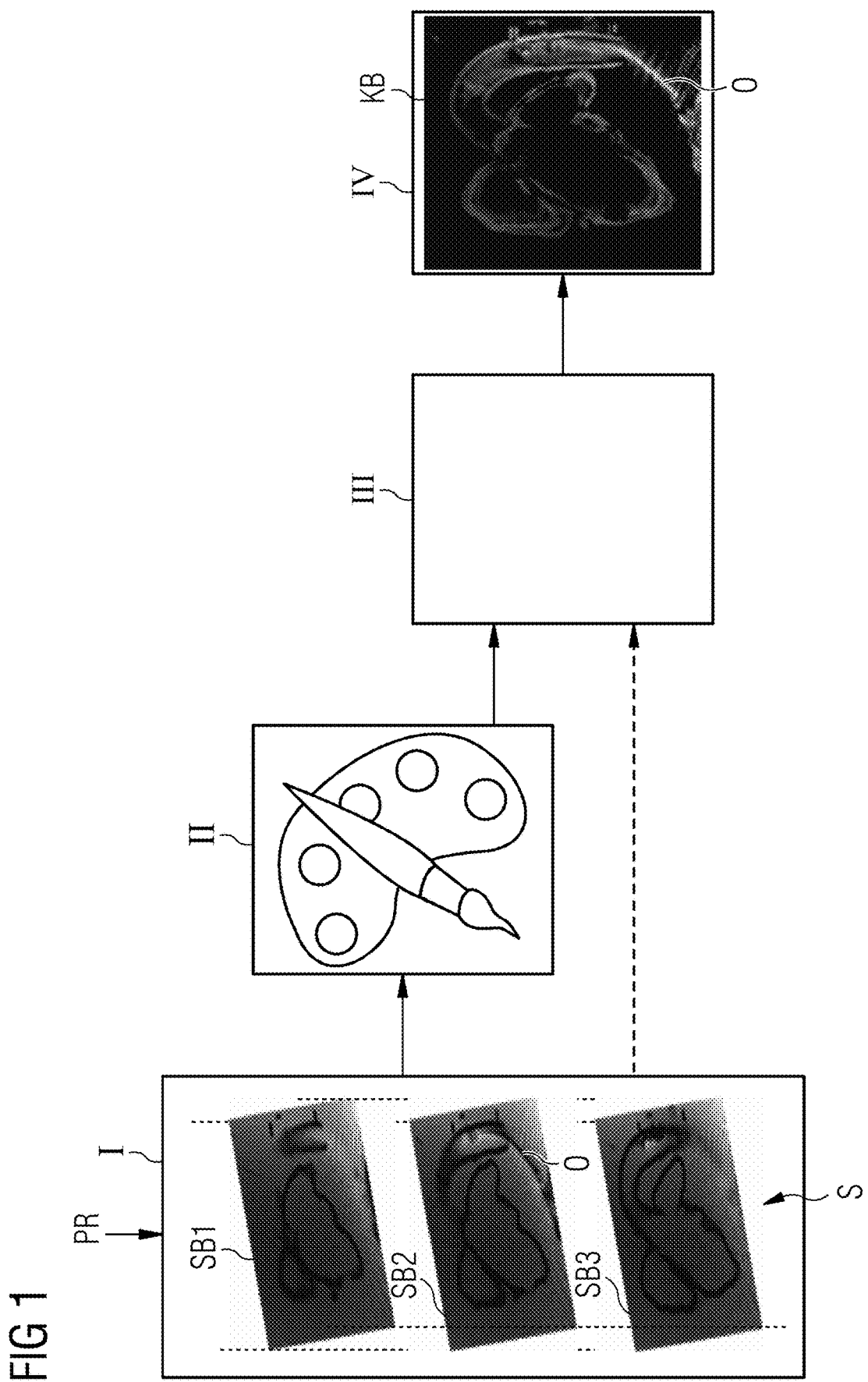
FIG. 1 is a flowchart that shows an example of a preferred embodiment of the method according to the invention.

In the example of a preferred course of a method shown in FIG. 1, in step I a stack S composed of three sectional images SB1, SB2, SB, SB3 representing adjacent, parallel sections through a heart, is provided. In the middle sectional image SB2, the medical object O can be seen in the bottom right corner.

Arrows are intended to elucidate the further processing of the data, wherein dashed arrows symbolize optional processing.

Figure 2:
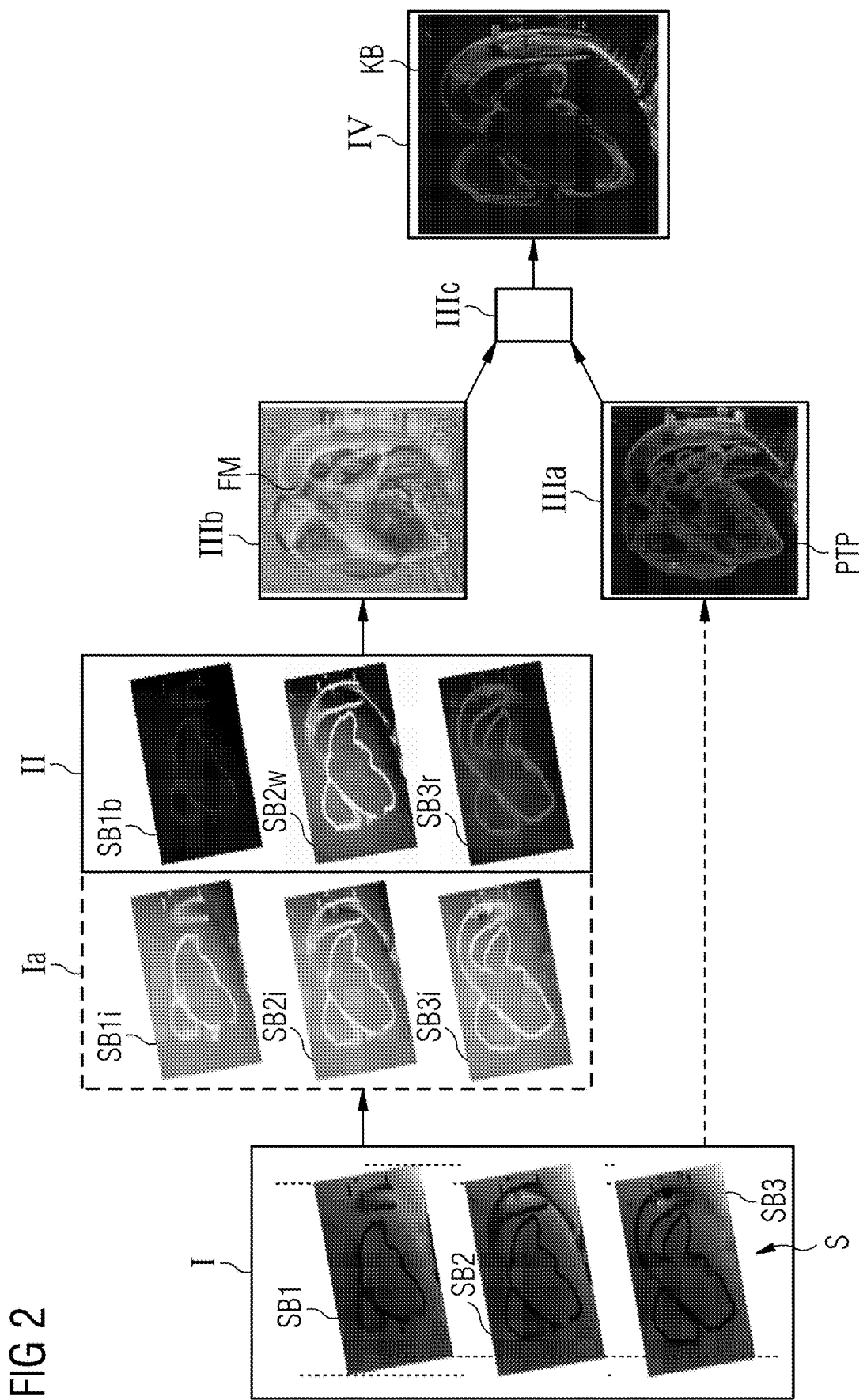
FIG. 2 is a more detailed flowchart of a preferred specific embodiment of the method according to FIG. 1.

In step II, the above-described color coding of the sectional images takes place, as the palette depicted is intended to elucidate. Step II of the more detailed FIG. 2, shows in this regard that each sectional image, or the pixels thereof, is given individual color labeling. For example, the uppermost sectional image can be colored blue, the middle sectional image can be colored white and the lowermost sectional image can be colored red, as shown in FIG. 2.

As shown in FIG. 2, optionally, before the color coding, inversion of the sectional images can take place in an intermediate step Ia and the inverted sectional images SB1$i$, SB2$i$, SB3$i$ can be color coded resulting in the color coded sectional images SB1$b$ (blue), SB2$w$ (white), SB3$r$ (red) in FIG. 2. In this case, this inversion produces enhanced highlighting of the contours. In theory, further graphical preprocessing is possible, for example sharpening of the edges.

Now, in step III, combination takes place to form a combination image KB. In this case, the projection direction is, as shown in FIG. 1 on the stack S, orthogonal to the plane of the sectional images SB1, SB2, SB3. Hence, pixels at the same sectional image coordinates are each combined with one another and produce a pixel in the combination image KB or first in a mask image FM, as depicted in Step IIIa in FIG. 2.

In the specific embodiment shown in FIG. 2, the combination step III according to FIG. 1 comprises three sub-steps IIIa, IIIb and IIIc.

In step IIIa, the original sectional images SB1, SB2, SB3 are accessed directly and a peak-to-peak-projection image PTP is created. In theory, it would also be possible to use the inverted sectional images SB1$i$, SB2$i$, SB3$i$ for this. This highlights the maximum differences in the intensities of the pixels of the individual sectional images SB1, SB2, SB3. Regions with many differences are depicted lighter than regions with fewer differences. However, this peak-to-peak-projection image PTP does not contain any information as to which of the sectional images SB1, SB2, SB3 has the greatest intensity or which of the sectional images SB1, SB2, SB3 exerts the greatest influence on the respective peak-to-peak value of an image coordinate.

This information is obtained from the mask image FM, which, in step IIIb, is created from the color coded sectional images SB1$b$, SB2$w$, SB3$r$. In the color mask image FM, the intensity of each pixel is standardized to a common value and each pixel contains the color values of the pixels of the sectional images SB1$b$, SB2$w$, SB3$r$ proportionally. Hence, this color mask image FM indicates which pixel of a sectional image SB1, SB2, SB3 is dominant in each case.

In step Inc, the peak-to-peak projection image PTP is combined with the color mask image FM. This is preferably performed by pixel-by-pixel multiplication of the respective intensities. The peak-to-peak projection image PTP is thereby colored according to the intensities in the individual sectional images.

Finally, in Step IV in FIGS. 1 and 2, the calculated combination image KB is output.

Figure 3:
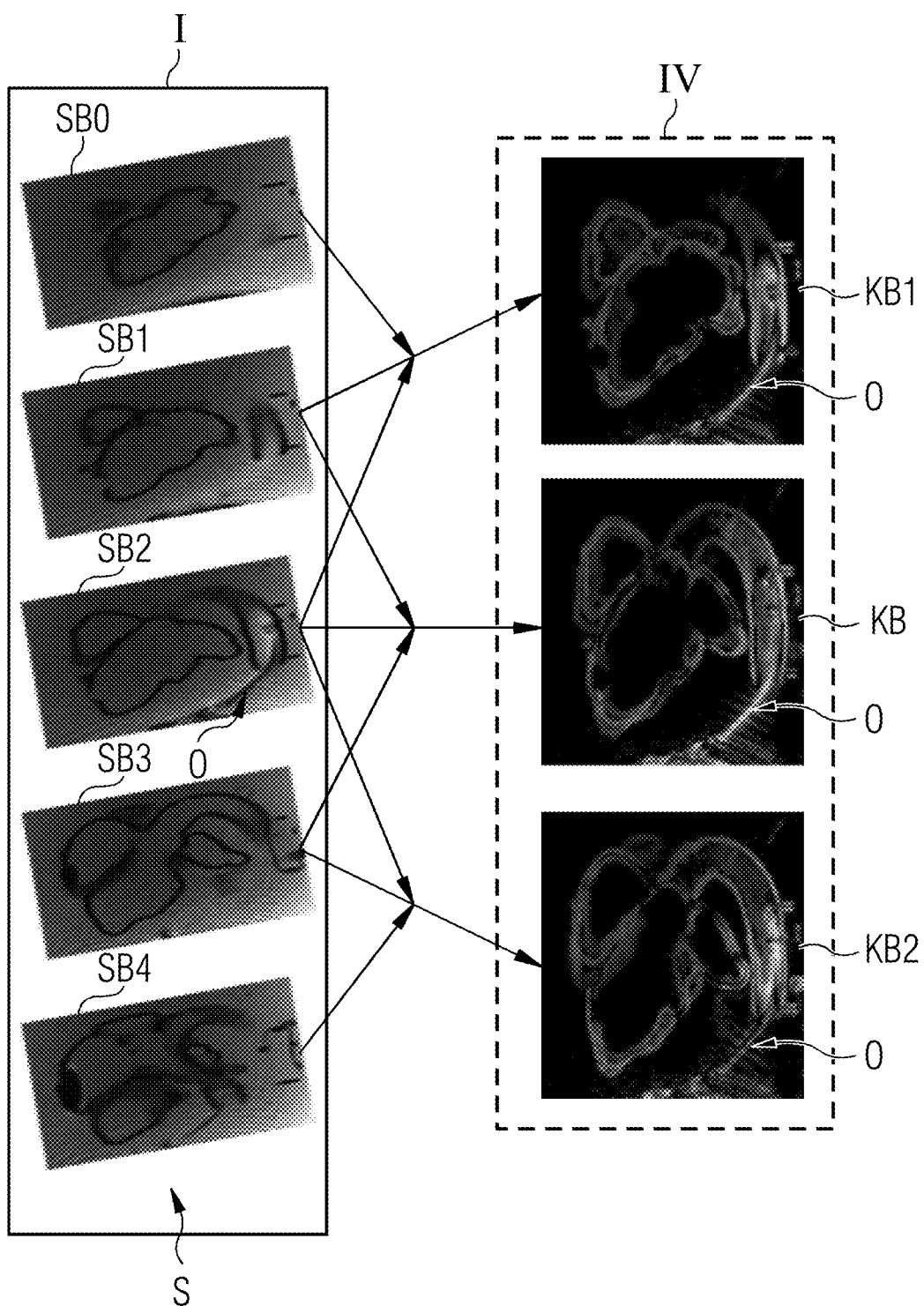
FIG. 3 is a simple flowchart for the formation of different combination images from in each case a selection of three sectional images from a total of five sectional images.
Figure 4:
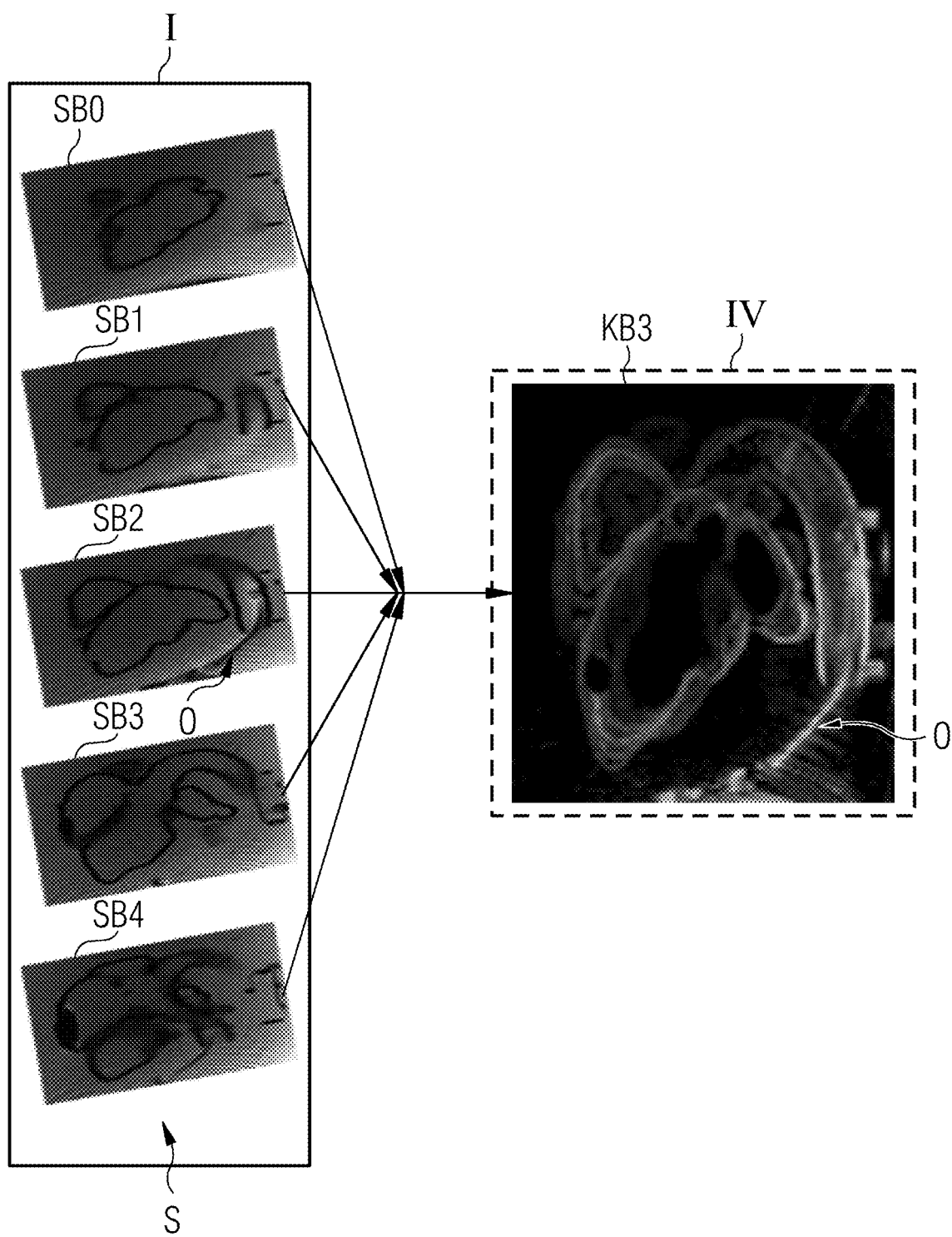
FIG. 4 is a simple flowchart for the formation of a combination image from the five sectional images in FIG. 3.

It is not mandatory for three sectional images SB1, SB2, SB3 to be recorded. In principle, two sectional images are also sufficient. However, as shown in FIGS. 3 and 4, it is also possible for a plurality of sectional images SB0, SB1, SB2, SB3, SB4 to be recorded. From these sectional images, it is possible to create a number of different combination images KB1, KB, KB2 in each case from three sequential sectional images SB0, SB1, SB2, SB3, SB4, as shown in FIG. 3, which is very suitable for localization of the medical object O.

For localization or detection of the medical object, the user can use the different combination images KB1, KB, KB2 and see in which of the combination images KB1, KB, KB2 the medical object O has a coding, here a color, indicating that it is located in the interior of the stack. This stack is then selected. It is possible to scroll through the individual combination images KB1, KB, KB2 relatively quickly and without complications. For subsequent tracking of the medical object, it is possible to select the setting of the selected stack, i.e. the settings which were used for recording the relevant sectional images of this stack. For example, for the respective combination images KB1, KB, KB2, the codings for the sectional images are selected such that the uppermost sectional image in the sub-stack under consideration was always coded blue, the lowermost always coded red and the middle always coded white. Then, advantageously the combination image KB selected is that with which the medical object is shown as white, i.e. lies in the middle.

FIG. 3 shows that, for a better comparison of the combination images KB1, KB, KB2, it is useful for the sectional images used for this always to be coded such that the same positions always have the same coding. For example, sectional image SB2 is colored red for the creation of the upper combination image KB1, colored white for the creation of the middle combination image KB and colored blue for the creation of the lower combination image KB2.

Similarly, the sectional images SB0, SB1, SB2, SB3, SB4 shown initially in FIG. 3 can also be combined to form one single combination image KB3, as shown in FIG. 4.

FIG. 4 shows that, for a better comparison of combination images KB1, KB, KB2, it is useful for all the section images used therefor to be coded differently, or at least the two outermost sectional images SB0 (for example blue) and SB4 (for example red), so that the departure from the stack by the medical object O can be reliably recognized from its coloring. In theory, the internal sectional images SB1, SB2, SB3 could all be coded similarly, for example white or no coloring. However, preferably, it is also possible to select a color progression, as described above. For example, in the case of five sectional images, the coding progression is blue for the uppermost sectional image, then light blue, followed by white for the middle sectional image, then light red and finally red for the lowermost sectional image.

Figure 5:
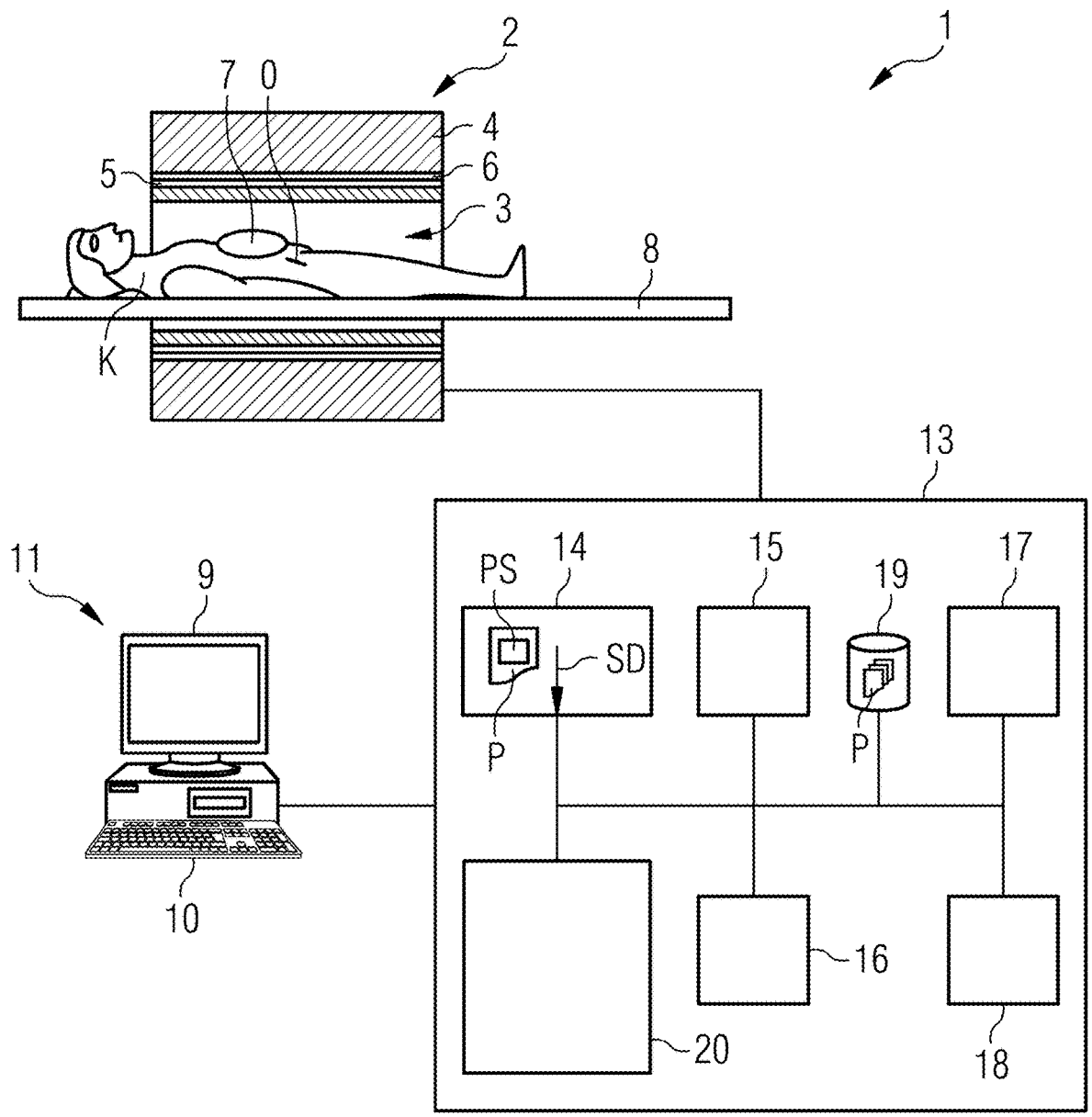
FIG. 5 schematically illustrates a magnetic resonance imaging system according to an exemplary embodiment of the invention.

FIG. 5 is a schematic representation of a magnetic resonance system 1. It comprises, on the one hand, the actual magnetic resonance scanner 2 or magnetic resonance imaging system 2 with an examination volume 3 or patient tunnel in which a patient or test subject is positioned on a bench 8 and in the body K of whom is located the actual medical object O, here a catheter O, which is to be visualized during the course of the method according to the invention.

The magnetic resonance scanner 2 is typically equipped with a basic field magnet 4, a gradient system 6, an RF transmission antenna 5 and an RF reception antenna 7. In the exemplary embodiment depicted, the RF transmission antenna system 5 is a whole-body coil permanently installed in the magnetic resonance scanner 2, while the RF reception antenna 7 is formed by local coils to be arranged on the patient or test subject (in this figure, only symbolized by one single local coil). In principle, however, the whole-body coil can also be used as the RF reception antenna and the local coils as an RF transmission antenna, as long as these coils can each case be switched to different operating modes. Here, the basic field magnet 4 typically generates a basic magnetic field in the longitudinal direction of the patient, i.e. along the longitudinal axis of the magnetic resonance scanner 2 extending in the z direction. The gradient system 6 typically has individually controllable gradient coils in order to be able to switch gradients in the x, y or z directions independently of one another. The magnetic resonance scanner 2 also contains shim coils (not shown), which can be designed conventionally.

The MR system shown in FIG. 5 is a whole-body system with a patient tunnel into which a patient can be completely introduced. In principle, however, the invention can also be used with other MR systems, for example those with a laterally open C-shaped housing. The only essential factor is that it is possible to prepare appropriate recordings of the medical object O. This enables the object, which can, for example, be a catheter, to be tracked with respect to its progression and its movement in the body, including during an "online" examination, i.e. virtually in real time.

The MR system 1 furthermore has a central control computer 13 that controls the MR system 1. This central control computer 13 includes a sequence controller 14. This controls the sequence of radio-frequency pulses (RF pulses) and gradient pulses in dependence upon a selected pulse sequence PS or a train of a number of pulse sequences for recording a plurality of slices in a volume region of interest of the examination object during a scanning session. Such a pulse sequence PS can be specified and parameterized in a scan or control protocol P. Different control protocols P for different scans or scanning sessions are typically stored in a memory 19 and can be selected by an operator (and optionally changed if required) and then used to carry out the scan.

To emit the individual RF pulses of a pulse sequence PS, the central control computer 13 has a radio-frequency transmitter 15 that generates and amplifies the RF pulses and outputs them via a suitable interface (not shown in detail) into the RF transmission antenna system 5. To control the gradient coils of the gradient system 6 in order to switch the gradient specified pulse sequence PS suitably, the control computer 13 has a gradient system interface 16. The sequence control computer 14 communicates in a suitable manner, for example by emitting sequence control data SD, with the radio-frequency transmitter 15 and the gradient system interface 16 for executing the pulse sequences PS.

The control computer 13 also has a radio-frequency receiver 17 (which also communicates in a suitable way with the sequence control unit 14) in order to receive magnetic-resonance signals inside the readout window specified by the pulse sequence PS and coordinated by means of the RF reception antenna system 7 and thus to acquire the raw data.

Here, a reconstruction computer 18 accepts the acquired raw data and reconstructs magnetic-resonance image data therefrom. This reconstruction also generally takes place on the basis of parameters that can be specified in the respective scan or control protocol P. This image data can then be stored in a memory 19.

The details of how suitable raw data can be acquired and MR images (magnetic resonance images, i.e. the sectional images required for the method) reconstructed therefrom by the irradiation of RF pulses and the switching of gradient pulses are known in principle to those skilled in the art, and thus need not be explained in more detail herein.

The required sectional images can then be sent to an evaluation processor 20, which here includes the visualization apparatus 212 for carrying out the method according to the invention. The visualization apparatus 21 and the evaluation processor 20 are shown in more detail in FIG. 6.

Figure 6:
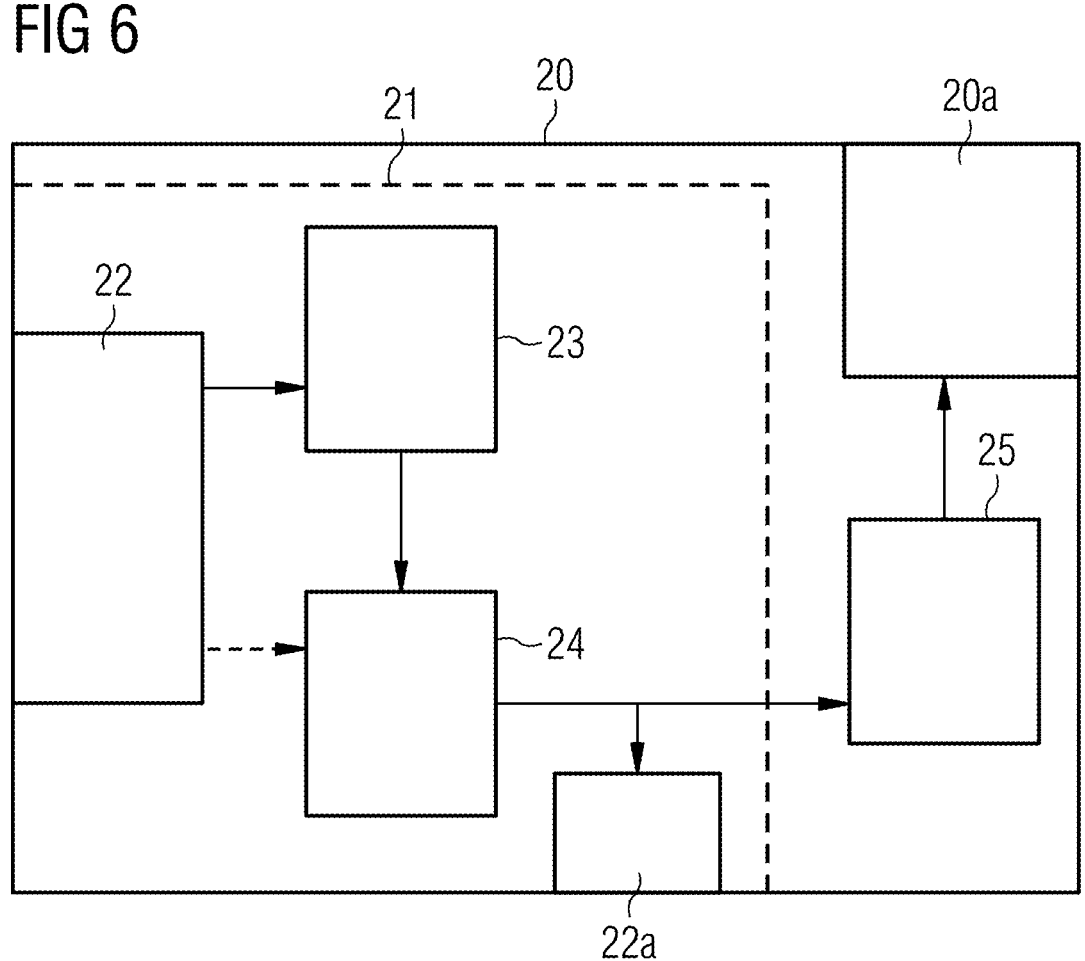
FIG. 6 schematically illustrates the evaluation processor in FIG. 5.

The visualization apparatus 21 has an image interface 22 for receiving the sectional images, an image output interface 22a for emitting the combination images KB, a coding processor 23 for the individual coding of the sectional images and an image-creating processor 24 for the creation of the combination images. The arrows in FIG. 6 represent data flows. For example, both the coding processor 23 and the image-creating processor 24 can access the image interface 22 in order to obtain sectional image data; however, it is also possible for the image-creating processor 24 to obtain its data solely from the coding processor, as is indicated by a dashed arrow from the image interface 22.

All the units of the visualization apparatus 21 can be present in the form of software modules.

The evaluation processor 20 optionally has a recognition processor 25, which can also be present as an independent unit in the control computer 13 or part of the visualization apparatus 21. This recognition processor 25 automatically recognizes the medical object O, and optionally via the coding thereof and the known position of the planes of the sectional images SB1, SB2, SB3, also the orientation thereof relative to the sectional images and generates information as to how the positioning, and optionally also the alignment, of the slice planes should be changed for a further recording of a new stack S of sectional images.

The recognition processor 25 can also be present as a software module.

Here, the data required for this, for example the coordinates of the new desired slice positions (optionally also only defined relative to the present slices) is sent by the control interface 20a to the other components of the control computer 13, in particular the sequence controller 14.

The central control computer 13 can be operated via a terminal 11 with an input unit 10 and a display unit 9 via which the entire MR system 1 can thus also be operated by an operator. MR images can also be displayed on the display unit 9 and scans can be planned and started and in particular control protocols P selected and optionally modified by the input unit 10, optionally in combination with the display unit 9.

Similarly, the combination images KB can be shown on the display unit 9 of the terminal 11 and the recording of sectional images controlled based on the information in the combination images KB.

The visualizing apparatus 21 or the evaluation processor 20 do not mandatorily have to be part of the control computer 13. For example, one or both components can also be provided in an evaluation computer or a diagnostics station, which are, for example, connected to the control computer 13 via a radiological network. However, it is advantageous for these components to be directly present in the control computer 13 since this facilitates quick and uncomplicated tracking and online monitoring during the intervention.

In addition, the magnetic resonance imaging system 1 according to the invention, and in particular the control computer 13, have numerous further components, not described here in detail, but which are typically present in such systems, such as, for example, a network interface in order to connect the entire system to a network and to enable the exchange of raw data and/or image date or parameter maps, and also further data, such as, for example, patient-relevant data or control protocols.

Finally, it is noted once again that the method described in detail above and the magnetic resonance imaging system are only exemplary embodiments and can be modified by the person skilled in the art in wide ranges without departing from the scope of the invention. Furthermore, the use of the indefinite article "a" or "an" does not preclude the possibility that the features in question may also be present on a multiple basis. Similarly, the terms "unit" and "module" do not preclude the possibility of the components in question consisting of a plurality of interacting partial components, which could also be spatially distributed.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for visualizing a position of a medical object in a body of a patient, comprising:
    providing a processor with a stack of sectional images acquired in succession through the body of the patient by magnetic resonance imaging, at least some of said sectional images containing an image of at least a part of said medical object therein;
    in said processor, individually, sectional-image-specifically, coding at least some of the sectional images in said stack by giving pixels in each sectional image that is coded a sectional-image-specific coding that is unique, among the sectional images that are coded;
    in said processor, generating a combination image by combining a plurality of the coded sectional images from said stack; and
    displaying the combination image at a display in communication with said processor with the sectional-image-specific coding thereby allowing visual identification of the position of the medical object that is associated with at least one sectional image in which at least a part of said medical object is present.

2. A method as claimed in claim 1 wherein said sectional-image-specific coding is a color coding, with all pixels in a respective coded sectional image being given a color that is different from any other color given to any other sectional image in said stack.

3. A method as claimed in claim 1 comprising generating said combination image by applying a predetermined combination function to respective pixels in different ones of said sectional images that lie aligned along a predetermined projection direction, said combination function comprising an intensity-value-dependent projection.

4. A method as claimed in claim 3 comprising generating said combination image by generating a mask image from the coded sectional images that are combined with a projection image based on the respective sectional images before coding thereof.

5. A method as claimed in claim 1 comprising, in said processor, graphically processing the respective sectional images, before coding thereof, by applying a graphical operation thereto selected from the group consisting of edge enhancement, Hough transform, posterization, deflickering, soft focus, sharpening, inversion, brightness change, and contrast change.

6. A method as claimed in claim 1 comprising, in said computer, executing an automatic recognition algorithm in order to automatically recognize said medical object in said combination image.

7. A method as claimed in claim 6 comprising executing said automatic recognition algorithm based on a comparison selected from the group consisting of a comparison of the sectional images respectively with reference images, and a comparison based on a Hough transform.

8. A method as claimed in claim 6 comprising, in said processor, providing said processor with a further stack of sectional images of the body of the examination subject in which said medical object is present, and, in said processor, automatically tracking said medical object in said further stack of sectional images.

9. A method as claimed in claim 8 comprising, in said processor, aligning orientation of the respective sectional images so that an axis of said medical object having a largest extent, or a probable route thereof through said stack, proceeds in the respective planes of the sectional images, with said automatic tracking being implemented by seeking coding of the pixels representing the medical object that is as uniform as possible.

10. A method as claimed in claim 1 comprising, in said processor, graphically post-processing said combination image in order to improve a representation of the medical object therein, based on at least one post-processing assumption selected from the group consisting of there being no overlapping of structures of the medical object in two adjacent sectional images among the sectional images in said stack, that the medical object has a continuous contour, and that the medical object has a uniform gradient over a contour of the medical object.

11. A method as claimed in claim 1 comprising selecting said stack of sectional images so that an expected position of the medical object is situated in an interior of the stack and an orientation of the sectional images corresponds to an expected orientation of a longest extent of said medical object.

12. A visualization apparatus, comprising:
a processor and a display in communication with said processor;
said processor receiving a stack of sectional images acquired in succession through the body of a patient by magnetic resonance imaging, at least some of said sectional images containing an image of at least a part of a medical object therein;
said processor being configured to individually, sectional-image-specifically, code at least some of the sectional images in said stack by giving pixels in each sectional image that is coded a sectional-image-specific coding that is unique, among the sectional images that are coded;
said processor being configured to generate a combination image by combining a plurality of the coded sectional images from said stack; and
said processor being configured to display the combination image at said display with the sectional-image-specific coding thereby allowing visual identification of the position of the medical object that is associated with at least one sectional image in which at least a part of said medical object is present.

13. A non-transitory, computer-readable data storage medium encoded with programming instructions, said storage medium being loaded into a processor that is in communication with a display, and said programming instructions causing said processor to:
receive a stack of sectional images acquired in succession through the body of patient by magnetic resonance imaging, at least some of said sectional images containing an image of at least a part of a medical object therein;
individually, sectional-image-specifically, code at least some of the sectional images in said stack by giving pixels in each sectional image that is coded a sectional-image-specific coding that is unique, among the sectional images that are coded;
generate a combination image by combining a plurality of the coded sectional images from said stack; and
display the combination image at said display with the sectional-image-specific coding thereby allowing visual identification of the position of the medical object that is associated with at least one sectional image in which at least a part of said medical object is present.

* * * * *